United States Patent [19]

Misato et al.

[11] Patent Number: 4,599,233
[45] Date of Patent: Jul. 8, 1986

[54] AGRICULTURAL AND HORTICULTURAL FUNGICIDE AND FRUIT STORAGE DISEASE PREVENTING AGENT AND PROCESS FOR PRODUCTION THEREOF

[75] Inventors: Tomomasa Misato, Tokyo; Yasuo Homma, Sakado; Yutaka Arimoto, Urawa; Tohoru Hidaka, Ichikawa; Mitsuhara Yuda, Hirakata, all of Japan

[73] Assignees: Rikagaku Kenkyusho, Wako; Riken Vitamin Oil Co., Ltd.; Hodogaya Chemical Co., Ltd., both of Tokyo, all of Japan

[21] Appl. No.: 680,815

[22] Filed: Dec. 12, 1984

Related U.S. Application Data

[63] Continuation of Ser. No. 514,850, Jul. 18, 1983, abandoned, which is a continuation of Ser. No. 378,502, May 17, 1982, abandoned, which is a continuation of Ser. No. 223,708, Jan. 9, 1981, abandoned, which is a continuation of Ser. No. 55,553, Jul. 9, 1979, abandoned.

[30] Foreign Application Priority Data

Jul. 13, 1978 [JP] Japan .................................. 53-85326

[51] Int. Cl.$^4$ ............................................. A01N 59/00
[52] U.S. Cl. ................................................... 424/127
[58] Field of Search ........................................ 424/127

[56] References Cited

U.S. PATENT DOCUMENTS 2,433,123 12/1947 Hudson ............................... 424/321
4,018,926 4/1977 Wommack ........................... 424/258
4,034,104 7/1977 Daum et al. ......................... 424/289

OTHER PUBLICATIONS

Gregory, Uses & Applications of Chemicals and Related Materials, pp. 26–27, 1944.

*Primary Examiner*—Leonard Schenkman
*Attorney, Agent, or Firm*—Bucknam and Archer

[57] ABSTRACT

It was found that sodium bicarbonate has a fungicidal activity and at the same time that the compound has a defect as a fungicide in that it is inferior in adhesiveness and spreadability and for this reason cannot be used alone as a fungicide. It is further found that an agricultural and horticultural fungicide having lasting fungicidal activity against plant diseases in a control value of over 90% can be obtained by using sodium bicarbonate in combination with a surfactant, particularly a food emulsifier, and further that the combination shows extensive effect in preventing fruit storage diseases. As all components of the combination are substances approved as food additives throughout the world, the fungicide does not cause pollution or present any hazard to human health.

12 Claims, No Drawings

AGRICULTURAL AND HORTICULTURAL FUNGICIDE AND FRUIT STORAGE DISEASE PREVENTING AGENT AND PROCESS FOR PRODUCTION THEREOF

This is a continuation application of Ser. No. 514,850 filed July 18, 1983 which was a continuation of Ser. No. 378,502 filed May 17, 1982, which was a continuation of Ser. No. 223,798 filed Jan. 9, 1981, which was a continuation of Ser. No. 055,553 filed July 9, 1979 all abandoned.

BACKGROUND OF THE INVENTION

The present invention relates to an agricultural and horticultural fungicide and fruit storage disease preventing composition and a process for production thereof.

Heretofore, heavy metal compounds such as copper, mercury or arsenic compounds, organic chlorine compounds, and organic phosphoric acid compounds have widely been used as fungicide, but these chemicals are harmful to the human body and animals, contaminate the soil and thus pose a serious problem in connection with environmental pollution.

Under such circumstances, there has been a pressing need for a safe agricultural and horticultural fungicide which has no ill-effects on humans body and animals.

In fact, however, no satisfactorily safe fungicide has yet been found for use with garden products and fruit trees, especially for use with vegitables and fruits which are merely washed with water before eating.

In view of such state of the art, the inventors of the invention carried out an extensive study on the development of highly safe and effective drugs for plant diseases and have found that sodium bicarbonate has a high fungicidal effect on plant diseases. This discovery led to the accomplishment of the present agricultural and horticultural fungicide which contains sodium bicarbonate as one effective component.

Although sodium bicarbonate is a very well-known and wery safe compound which is widely used as a medicaments and in food blowing agents such as baking powder, its fungicidal effect has not heretofore been known.

Sodium bicarbonate cannot, however, be used alone as a fungicide because it is inferior in adhesiveness and spreadability. Moreover, in a liquid form such as aqueous solution, it has a high surface tension and does not attach to the plant body well enough to manifest satisfactory fungicidity.

Accordingly, the inventors considered combined use of sodium bicarbonate with a surfactant and as a result of this study they found that there are certain limitations on the surfactants that can be used with sodium bicarbonate. These limitations derive from the fact that sodium bicarbonate exhibits alkaline behavior in an aqueous solution and, because of this, exhibits poor compatability with some surfactants.

In spite of the difficulty in finding suitable surfactants, the inventors continued their study because they were well aware of the tremendous advantages to be obtained if sodium bicarbonate could be used as a fungicide on vegetables or fruits. Their study eventually resulted in the development of a non-polluting fungicide comprising sodium bicarbonate in combination with food emulsifiers used as the surfactants.

It was found that food emulsifiers themselves exhibit fungicidal effect, albeit weakly. When a food emulsifier is used together with sodium bicarbonate, the two chemicals show excellent compatibility. Moreover, the composition is easy to apply to plants and displays not only good adhesiveness but also a synergistic fungicidal action resulting in a control effect over 90% against etiological cause of a plant diseases and fruit storage diseases.

SUMMARY OF THE INVENTION

As described above, the inventors have determined that co-use of sodium bicarbonate and a food emulsifier decreases the surface tension of sodium bicarbonate and significantly improves its adhesiveness and spreadability with respect to plants and further that the combination produces a synergistic effect which enhances the fungicidal properties of the two chemicals. Thus by combining the two chemicals there is obtained a composition having excellent effects in preventing plant and fruit diseases. Furthermore, it has been clarified that the combination is exceedingly safe in that it has no ill effects on humans or an animals and plants.

Accordingly, the object of the invention is to provide an agricultural and horticultural fungicide and fruit storage disease preventing agent comprising sodium bicarbonate and food emulsifiers as effective components.

Another object of the invention is to provide a process for producing the above mentioned fungicide wherein the dispersability of a food emulsifier with low dispersability in the dispersing medium, which may in many cases be water, is improved.

A further object of the invention is to provide a non-polluting agricultural and horticultural fungicide and fruit storage disease preventing agent.

Still further objects of the invention will be clear to those skilled in the art from the following descriptions.

The present fungicide is effective against every kind of plant disease but has particularly excellent effect against the plant diseases and storage diseases of vegetables and fruits. It has excellent effect, for example, against plant diseases effecting such vegetables as cucumbers, eggplants, tomatoes, etc., such vegetables as Spanish paprika, lettuce, parsley, celery, cabbage etc. which are eaten raw, such pulses as kidney beans, green soy-beans etc. and such fruits as strawberries, lemons, apples, oranges, grapes, melons etc.

DETAILED DESCRIPTION OF THE PREFERRED EMBODIMENTS

As mentioned in the above, the present invention provides a non-polluting agricultural and horticultural fungicide and fruit storage disease preventing agent which comprises sodium bicarbonate and food emulsifier as essential components, and the process for production thereof.

The effects induced by mixing the two components derive from the improvement in the adhesiveness and spreadability on the plant bodies resulting from the decrease in surface activity attributable to the affinity of the two components which overcomes the alkaline behavior of the sodium bicarbonate and from the fungicidal effects synergistically induced from the fungicidal activities of the two components.

Furthermore, the fungicidal effect obtained is sustained continuously and stably. For example, in the case of citrus fruits, the means preventing value of sodium bicarbonate is 60% for a single use but tends to decrease as the disease breaks out and becomes wide spread. On the contrary, in the case of using a mixture of the two components, a stable preventing effect is obtained and a preventing value over 90% is again manifested at the time of an outbreak of the disease. Similar results were also obtained for the diseases of the vegetables.

Since in the invention are used food emulsifiers which are recognized being safe and presenting no hazard to animal or plant life, the invention provides a non-polluting agricultural chemical useful as a fungicide and storage disease preventing agent having no adverse effect on the human body.

If necessary, adjurants having high safety such as approved food additives may be used in the fungicide of this invention without causing any detrimental effect on the humand body.

Accordingly, no special precautions need be taken in the spraying of the present fungicide and storage disease preventing agent and the vegetables and fruits which have been sprayed with the present composition can be used as food after being simply washed with water. Even if the vegetables and fruits are not washed adequately and retain a small amounts of the present composition, they will have no adverse effect on the person eating them.

Some examples of diseases preventable by using the present fungicidal composition are as follows:
Powdery mildew: cucumber, egg-plant, melon, strawberry, Spanish paprika and the like.
Anthracnose: cucumber, grape, orange and the like.
Downy mildew: cucumber, potato, tomato and the like.
Leaf mold: tomato and the like.
Ripe rot: grape and the like.
Scab: oranges and the like.
Mold caused by Genus Penicillium: blue mold and common green mold of oranges and the like.
Rice blight: blast, sheath blight, helminthosporium leaf spot and the like.

Food emulsifiers are classified as food additives and are strictly regulated by the Food Sanitation Laws etc. of countries throughout the world. Thus, in any given country, only those additives which have been approved can be used in foods. Some of these additives have been approved for use in virtually every country since it has been found that they have no bad effect on humans. Among them universally approved compounds, are lecithin (natural product), several kinds of fatty acid esters, and small number of soaps (metal salts of fatty acids).

Among the fatty acid esters, there are fatty acid glycerol esters, fatty acid sucrose esters, fatty acid sorbitan esters and fatty acid propylene glycol esters.

The fatty acid components used in the above-mentioned esters are called "edible fatty acids" and usually comprise saturated or unsaturated fatty acid having carbon numbers between 6 and 22. Approved edible fatty acids include, for example, saturated fatty acids such as caproic acid, capric acid, caprylic acid, lauric acid, myristic acid, palmitic acid, stearic acid, arachic acid, behenic acid, arachidic acid and the like, unsaturated acids such as oleic acid, linoleic acid, linolenic acid, ricinoleic acid, arachidonic acid, erucic acid and the like and mixtures thereof, and other fatty acids derived from animal and vegetable fat and oil such as tallow, fish oil, soy-bean oil, cotton seed oil, rape seed oil, palm oil, coconut oil etc. and the hydrogenated oils thereof.

Typical food emulsifiers will now be described in detail.

Among glycerides, there are monoglycerides which are mono-esters of glycerol with the above-mentioned edible fatty acids, derivatives of the mono-glycerides which are esters of the monoglycerides with monobasic, dibasic or tribasic fatty acids such as acetic acid, lactic acid, tartaric acid, citric acid and the like, ethyleneoxide condensates of the said monoglycerides, the esters of polyglycerol such as diglycerol ester.

However, the fatty acids of glycerol are usually mixtures. For example, mono-esters of fatty acid and glycerol contain a small amount of di- or tri-ester, and the purity of purified monoester is in almost 90%. However, any of these may be used in the present invention.

Commercially available fatty acid sucrose ester is a mixture of mono- and di-ester and sucrose. It is highly hydrophilic and has excellent properties as a wetting agent.

Fatty acid sorbitan esters are mixed esters, since sorbitan itself is an inner-dehydration product of solbitol and a mixture of 1.4-worbitan, 3.6-sorbitan, 1.5-sorbitan and further inter molecular dehydration product such as 1,4 3,6-sorbid. Several kinds of fatty acid sorbitan esters are commercially available under the commercial name of "Span" and are used as food emulsifiers.

Ethyleneoxide condensates of fatty acid sorbitan esters are commercially available under the name of "Tween" which is used as food emulsifier in the United States etc.

The crude fatty acid propyleneglycol ester contains di-ester and propylene glycol. It is purified by molecular distillation. Any of these may be used in this invention.

Lecithin is a natural emulsifier which, in the process of purifying soy-bean oil, is obtained in a mixture with oil or fat, organic carboxylic acid, sterol etc. as a transparent or opaque sticky substance. It is also available as a purified substance in powdered form. Either form may be used in this invention. Hydroxylated lecithin with increased solubility in water is also available.

As the metal salts of fatty acids, there are used potassium, sodium or calcium salts of the edible fatty acids, for example, calcium or sodium stearoyl lactylate, or potassium, sodium or calcium salt of edible fatty acids.

The food emulsifiers used in this invention can be used in their commercially available form or after purifying, and further they can be used in mixtures of two or more kinds thereof.

The food emulsifiers enumerated above are mentioned only for illustration without any intention to limit the invention. Any kind of food emulsifier which has been approved in the country in which the composition is to be employed can be used in this invention.

Regardless of whether the food emulsifier is in the liquid, wax or solid state, it can be formulated into a wettable powder, dust or granular substance by mixing with sodium bicarbonate.

Various methods can be used to prepare the compositions according to this invention. For example, in one method one or more food emulsifiers are mixed, melted and then mixed with sodium bicarbonate. In another method, one or more emulsifiers are dissolved in a solvent or mixed-solvent approved as food additives such as alcohol, propyleneglycol or sorbitol and the solution is sprayed onto or mixed with sodium bicarbonate particles to coat the crystal particles thereof with the food emulsifier to obtain a dust or wettable powder.

In order to formulate these preparations more easily, after emulsifying or dispersing the food emulsifier into warm water in the presence of hydrophilic colloidal substances which have been approved as food additives such as starch, dextrine, alginic acid and salts thereof, carboxymethylcellulose, sodium caseinate, the obtained solution is dried into a powder by a suitable drying method such as spray drying, foam drying, freeze drying, drum drying etc. to obtain a food emulsifier powder easily dispersable in cold water, and the obtained powder is mixed with sodium bicarbonate powder to obtain wettable powder, dust etc.

In this method, the hydrophilic colloidal substance is used in an amount corresponding to 5 to 50 percent by weight of the total weight, preferably 5 to 30 percent by weight. To disperse them into warm water, are used 30 to 60 percent by weight of total amounts of said colloidal substance and food emulsifier.

A suitable carrier such as clay, white carbon, distomaceous earth, kaolin, talc, silica, calcium carbonate etc. may be added to the dust or wettable powder of the invention. Although these carriers are not approved food additives, they can be easily removed by washing, and further the existence of these substances can be easily ascertained visually. Therefore the use of these carriers in the invention presents no health hazard.

According to circumstances, the present composition may be mixed and used with other conventional adjurants such as spreader, wetting agent, adhering agent and the like. These surfactants are effective in enhancing the wettability of the effective components of the invention, and thus adjunants as alkylaryl sulfonate and polyoxyalkylaryl sulfonate may be conveniently mixed in and be used as in the case of conventional agricultural chemicals.

Furthermore, similarly to this, other agricultural chemicals such as fungicides, insecticides, plant growth controlling agent and herbicides may be suitably mixed with the present composition and used so far as these chemicals do not decrease the fungicidal effects of the present fungicide.

The total amount of the effective components is 10 to 100 percent by weight in the wettable powder and 0.1 to 20 percent by weight in the dust, but these amounts can be increased or decreased according to the object of use.

The amount of the composition used to obtain satisfactory effects per 10 are is 150 to 400 l of a solution diluted into 150 to 300 folds with water in the case of the wettable powder and 3 to 9 kg of powder in the case of the dust.

The present invention will be explained by way of examples in the following, but these explanations are made only for illustration and not to limit the invention.

Parts in the following are parts by weight unless otherwise specifically indicated.

EXAMPLE 1

(wettable powder)

60 parts of sodium bicarbonate, 15 parts of sucrose laurate and 25 parts of white carbon were mixed and pulverized to obtain a wettable powder.

EXAMPLE 2

(wettable powder)

70 parts of sodium bicarbonate, 10 parts of sucrose mono-laurate and 10 parts of glycerol-mono-stearate tartarate and 10 parts of white carbon were mixed and pulverized to obtain wettable powder.

EXAMPLE 3

(dust)

20 parts of sodium bicarbonate, 10 parts of sucrose mono-myristate and 70 parts of a mixture of clay and talc were mixed and pulverized to obtain dust.

EXAMPLE 4

(wettable powder)

6 parts of glycerol monostearate and 4 parts of sorbitan monolaurate were dissolved in 10 parts of glycerol. The obtained solution was sprayed on 80 parts of fine particles of sodium bicarbonate under stirring to enhance the absorption of the solution by the sodium bicarbonate so as to obtain a wettable powder.

EXAMPLE 5

(wettable powder)

15 parts of diglycerine mono-linolate, 5 parts of propyleneglycol monooleate were dissolved in 5 parts of propyleneglycol, and the obtained solution was added to 75 parts of fine particles of sodium bicarbonate under stirring to obtain a wettable powder.

EXAMPLE 6

(wettable powder)

10 parts of sorbitan monostearate and 10 parts of polyoxyethylene (20)-sorbitan-monolaurate were dissolved in 5 parts of propyleneglycol and the obtained solution was added and, under stirring, absorbed by the fine particles of sodium bicarbonate to obtain a wettable powder.

EXAMPLE 7

(dust)

10 parts of sodium caseinate was dissolved in 150 parts of water. 80 parts of glycerol monostearate and 10 parts of sorbitan monooleate were melted together and added to the solution at temperature of 65° C. to produce a homogeneous solution. The solution was dried with a spray drier to obtain a powder easily dispersable in cold water and having good fluidity. 30 parts of the obtained powder, 70 parts of sodium bicarbonate and 400 parts of distomaceous earth were thoroughly mixed to obtain dust.

EXAMPLE 8

(wettable powder)

90 parts of glycerol mono-palmitate was mixed with a solution of 10 parts of CMC in 200 parts of water and was heated to a temperature of 65° C. to obtain a homogeneous solution. The solution was dried with a spray drier to obtain a powder easily dispersable in cold water and having good fluidity. A wettable powder was obtained by homogeneously mixing 40 parts of the obtained powder and 60 parts of sodium bicarbonate.

EXAMPLE 9

(wettable powder)

20 parts of sorbitan mono- and tri-oleate were dissolved in 5 parts of propyleneglycol, and the solution was mixed with and absorbed by 75 parts of fine particles of sodium bicarbonate under stirring to obtain a wettable powder.

EXAMPLE 10

(wettable powder)

30 parts of polyoxyethylene (20)-glycerol monosoybean oil fatty acid ester was mixed with 30 parts of finely devided cellulose crystal. The obtained mixture was further mixed with 30 parts of sodium bicarbonate to obtain a wettable powder.

EXAMPLE 11

(wettable powder)

10 parts of sodium caseinate was dissolved in 200 parts of water. 80 parts of glycerol mono-cotton seed oil fatty acid ester and 10 parts of sorbitan mono-stearate were mixed and melted together, and added to the solution and heated to a temperature of 65° C. to produce a homogeneous solution. The solution was dried with a spray drier to obtain powders easily dispersable in cold water and having good fluidity. 60 parts of the obtained powder was homogeneously mixed with 40 parts of sodium bicarbonate to obtain a wettable powder.

EXAMPLE 12

(wettable powder)

80 parts of sodium bicarbonate, 20 parts of highly purified lecithin (Lecion P) were thoroughly mixed and a wettable powder was obtained.

EXAMPLE 13

(dust)

20 parts of sodium bicarbonate, 10 parts of Lecion LP-1 and 70 parts of a mixture of talc and clay were thoroughly mixed and pulverized to prepare a dust.

EXAMPLE 14

(wettable powder)

80 parts of sodium bicarbonate, 10 parts of glycerol monostearate and 10 parts of white carbon were mixed and pulverized to prepare a wettable powder.

In the Examples in the above and in the Test Examples in the following, the following chemicals were used.

Sucrose monolaurate: DK-ester F 120, Daiichi Kogyo Seiyaku Co., Ltd. (Japan)
Sucrose mono-myristate: DK-ester F 140, ibid
Glycerol monostearate tartaric acid ester: Rikemal TS-100, Riken Vitamin Oil Co., Ltd. (Japan)
Glycerol monostearate: Rikemal S-100, ibid
Glycerol monopalmitate: Rikemal P-100, ibid
Glycerol monooleate: Rikemal OL-100, ibid
Glycerol mono-cotton oil fatty acid ester: Rikemal O-100, ibid
Polyoxyethylene (20) glycerol monostearate: Rikemal S-120, ibid
Diglycerine monolinorate: Rikemal R-71-D, ibid
Diglycerine monooleate: Rikemal O-71-D, ibid
Propyleneglycol monooleate: Rikemal PO-100, ibid
Sorbitan monostearate: Rikemal S-300, ibid
Lecion P: (highly purified lecithin), ibid
Lecion LP-1: a mixture of 70 wt.% of Lecion P and 30 wt.% of dextrine, ibid
Sorbitan monolaurate: Span 20, ICI
Sorbitan monooleate: Span 80, ICI
Sorbitan trioleate: Span 85, ICI
Polyoxyethylene (20 sorbitan monolaurate): Tween 20, ICI

TEST EXAMPLE 1

(Influence of varying the ratio of two components)

In pots having a diameter of 6.6 cm, two-week old cucumber seedlings (kind: Sagamihanpaku) were planted 3 seedlings per pot. Diluted wettable powders were prepared according to Example 14 and similarly to Example 14 but with increased and decreased amounts of glycerolmonostearate in the wettable powder, and further, at a higher concentration, the concentration of the wettable powder was diminished. By this procedure, the influence of the ratio of sodium bicarbonate and food emulsifier on the fungicidal effect of the composition was examined.

Namely, compositions having the concentrations shown in the following table were uniformly sprayed in an amount of 40 ml per two pots and dried. In a closed chamber, spores of cucumber plant powder midlew (*Sphaerotheca fullginea*) were artificially wind-inoculated. Five blocks of 25 pots each were treated.

After inoculation, the pots were placed in a greenhouse for 10 to 14 days, and the ratio of the occurence of infection was observed.

On the other hand, sodium bicarbonate and glycerol monostearate were used as controls and the degree of infection was likewise observed.

The preventing values were calcurated by the following formula.

$$\text{Preventing Value} = \frac{\text{Number of leisions in untreated area} - \text{Number of leisions in treated area}}{\text{Number of leisions in untreated area}} \times 100$$

The obtained results are shown in the following.

The preventing values in the following are mean values obtained from five blocks.

| Concentration (ppm) | | Preventing value (%) |
|---|---|---|
| Sodium bicarbonate | Glycerol monostearate | |
| 2000 | 0 | 62 |
| 2000 | 25 | 89 |
| 2000 | 50 | 92 |
| 2000 | 100 | 99 |
| 2000 | 200 | 100 |
| 2000 | 500 | 100 |
| 1000 | 200 | 95 |
| 500 | 200 | 68 |
| 250 | 200 | 23 |
| 0 | 200 | 15 |

TEST EXAMPLE 2

(Influence of varying the ratio of two components)

Test Example 1 was repeated except that sucrose laurate was used instead of glycerol monostearate. The following results were obtained.

| Concentration (ppm) | | Preventing value (%) |
|---|---|---|
| Sodium bicarbonate | Sucrose laurate | |
| 2000 | 0 | 62 |
| 2000 | 25 | 76 |
| 2000 | 50 | 85 |

-continued

| Concentration (ppm) | | Preventing value (%) |
|---|---|---|
| Sodium bicarbonate | Sucrose laurate | |
| 2000 | 100 | 92 |
| 2000 | 250 | 97 |
| 2000 | 500 | 99 |
| 1000 | 200 | 88 |
| 500 | 200 | 45 |
| 250 | 200 | 20 |
| 0 | 200 | 12 |

TEST EXAMPLE 3

(Influence of varying the ratio of two components)

Test Example 1 was repeated except that the wettable powder prepared according to Example 12 was used. The following results were obtained.

| Concentration (ppm) | | Preventing value (%) |
|---|---|---|
| Sodium bicarbonate | Lecion P | |
| 2000 | 0 | 62 |
| 2000 | 25 | 65 |
| 2000 | 50 | 73 |
| 2000 | 100 | 88 |
| 2000 | 200 | 96 |
| 2000 | 500 | 98 |
| 1000 | 200 | 92 |
| 500 | 200 | 52 |
| 250 | 200 | 26 |
| 0 | 200 | 5 |

Next, test examples are shown to illustrate the effect of the fungicidal compositions according to this invention in preventing many kinds of plant diseases.

TEST EXAMPLE 4

(Storage disease preventing test for oranges)

The peels of ten to twenty-five test oranges (kind: Unshu orange) were damaged by perforation to a depth of about 1.5 mm with a sewing needle. The oranges were damaged at five positions each, and 4 blocks were set up per composition for testing. After being damaged, the test oranges were spray inoculated at their damaged portions with a suspension of the spores of common green mold of oranges (*Penicillium digitatum*). After two hours, the test oranges were immersed in a diluted solution of the wettable powder prepared according to Example 1 for about five minutes. After drying, the test oranges were kept in an atmosphere having a relative humidity of 100%. After four to six days, the occurrence of the disease was observed. On the other hand, sodium bicarbonate and sucrose laurate were each used singly as controls and the tests were carried out in the same way. The damage caused by the disease was also observed. The preventing value was calculated according to the formula in Example 1. The results are shown in Table 1.

TABLE 1

| Test Compounds | Concentration ppm | Preventing value 4th day | 6th day | Chemical Injury |
|---|---|---|---|---|
| Sodium Bicarbonate | 2000 | 60 | 65 | none |
| Sucrose Laurate | 2000 | 20 | 18 | " |
| Sodium Bicarbonate + Sucrose Laurate | 2000 / 500 } 2500 | 95 | 100 | " |

The preventing values in Table 1 are mean values obtained in four blocks. In the case of using sodium bicarbonate or sucrose laurate alone, the preventing values obtained were so scattered that it was difficult to obtain stable means values. On the contrary, the preventing values of the present composition are concentrated in the range of over 95% and are stable.

TEST EXAMPLE 5

(Test for preventing powdery mildew in cucumber plants)

Two weeks old cucumber seedlings (kind: *Sagami hanpaku*) were planted in pots having a diameter of 6.6 cm, three seedlings per pot. The diluted solution of the wettable powder prepared according to Example 2 was uniformly sprayed on each pot in an amount of 40 ml per two pots. After drying, the pots were artificially wind-inoculated with spores of powdery mildew (*Sphaerotheca fullginea*) in a closed chamber. Five blocks were treated in the test, each block containing 25 pots.

After inoculation, the pots were kept in a greenhouse for 10 to 14 days to allow the disease to infect the seedlings. The speed of infection was observed.

The preventing values were calculated according to the formula in Example 1. The obtained results are shown in Table 2.

TABLE 2

| Test Compounds | Concentration (ppm) | Preventing Value 10th day | 14th day | Chemical Injury |
|---|---|---|---|---|
| Sodium Bicarbonate | 2000 | 40 | 35 | none |
| Sucrose Laurate | 2000 | 26 | 10 | " |
| Tartaric Acid Ester of Glycerol Monostearate | 2000 | 22 | 9 | " |
| Sodium Bicarbonate + Sucrose Laurate + Tartaric Acid Ester of Glycerol Monostearate | 2000 / 250 / 250 } 2500 | 95 | 93 | " |

The preventing values in Table 2 are mean values of those obtained in the five blocks. In the case of the use of sodium bicarbonate or sucrose laurate alone, there was large variation among the controlling values for the different blocks. In this point, there are found to be clear differences between the sole and combined of the present effective components. With the present composition, excellent and stable preventing values were obtained in each test block.

TEST EXAMPLE 6

(Test for preventing blast in rice plant)

In ten plastic pots of a diameter of 60 cm were planted ten rice plants seedlings (kind: Jukkoku) per pot. The seedlings were grown in a greenhouse. At the fourth leaf stage, the diluted wettable powder prepared according to Example 1 was sprayed on the rice plants with a spray gun in an amount of 40 ml per pot.

After drying, spores of rice blast (*Pyricularia oryzae*) which had been cultured in a chaff culture medium (comprising powdery enzyme, extract, soluble starch, sucrose, and chaff) were suspended in water and the suspension was uniformly sprayed on the rice plants. After inoculation, the rice plants were placed in an air conditioned box having a temperature of 27° C. and a relative humidity over 95% to be infected with the disease. Two days after infection, the number of leisions were counted. The preventing values were calculated according to the formulae in Example 1.

As control, sodium bicarbonate and sucrose monolaurate were used singly in the same way as above and the preventing values were also calculated for these.

The obtained results are shown in Table 3.

TABLE 3

| Test Compound | Concentration (ppm) | | Preventing Value (%) | Chemical Injury |
|---|---|---|---|---|
| Sodium Bicarbonate | 2000 | | 65 | none |
| Sucrose Laurate | 2000 | | 10 | " |
| Sodium Bicarbonate + | 2000 | 2500 | 98 | " |
| Sucrose Laurate | 500 | | | |

There are clear differences between the sole use of sodium bicarbonate or sucrose laurate and their combined use. The present fungicidal composition shows an excellent improvement in fungicidal effects over sole use of a single effective component.

TEST EXAMPLE 7

(Test for preventing stem end rot in orange plants)

New twigs of three years old orange plant seedlings (kind: Unshu orange) were used as test plant. New twigs were cut from an orange tree and planted. Then 10 to 20 granules of mixed fertilizer were applied. Two to three weeks after planting, the twigs were tested. Sterilized water was added to a culture medium of orange plant stem end rot (*Diaporthe citri*) to prepare a pycniospore suspension having a concentration of 200 spores per field of vision of a microscope at 150 magnifications. The twigs were inoculated with the suspension by spraying. After inoculation, the twigs were placed in wetted inoculation boxes for about 3 days. After the disease had become clearly visible, the twigs were transferred to a greenhouse.

The composition prepared according to Example 1 was diluted to a given concentration and sprayed uniformly on the pots in an amount of 40 ml per pot.

About 2 to 3 weeks after inoculation, the number of leisions were observed for all leaves on the twigs. The degrees of infection were divided into four groups by the number of leisions on the diseased leaf, namely 1 to 50 leisions (group 1), 51 to 150 leisions (group 2), over 151 leisions (group 3) and no leisions (0). The degrees of infection were calculated and then the preventing values were calculated from the said degrees of infection on the basis of the following formula.

$$\text{Degree of infection} = \frac{1 \times n_1 + 2 \times n_2 + 3 \times n_3}{3 \times N} \times 100$$

Wherein $n_1$, $n_2$ and $n_3$ respectively signify the number of leaves belonging in group 1, 2 and 3 mentioned above. N signifies the total number of leaves.

$$\text{Preventing Value (\%)} = \left( 1 - \frac{\text{Degree of infection in treated area}}{\text{Degree of infection in untreated area}} \right) \times 100$$

The obtained results are shown in the following table. On the other hand, sodium bicarbonate and sucrose laurate were used singly as controls in the same way as in the above and were also observed as to degree of infection.

TABLE 4

| Test Compounds | Concentration (ppm) | | Preventing Value (%) | Chemical Injury |
|---|---|---|---|---|
| Sodium Bicarbonate | 2000 | | 54 | none |
| Sucrose Laurate | 2000 | | 18 | " |
| Sodium Bicarbonate + | 2000 | 2500 | 89 | " |
| Sucrose Laurate | 500 | | | |

TEST EXAMPLE 8

(Test for preventing orange storage disease)

Test Example 4 was repeated except that sorbitan monolaurate glycerol monostearate and glycerol monooleate were used in the formulation in Example 8. The obtained results are shown in the following.

TABLE 5

| Test Compounds | Concentration (ppm) | | Preventing Value 4th day | Preventing Value 6th day | Chemical Injury |
|---|---|---|---|---|---|
| Sodium Bicarbonate | 2000 | | 60 | 55 | none |
| Sorbitan Monolaurate | 2000 | | 20 | 18 | " |
| Glycerol Monostearate | 2000 | | 15 | 8 | " |
| Glycerol Monooleate | 2000 | | 30 | 22 | " |
| Sodium Bicarbonate + | 1600 | 2000 | 100 | 96 | " |
| Sorbitan Monolaurate | 400 | | | | |
| Sodium Bicarbonate + | 1600 | 2000 | 100 | 95 | " |
| Glycerol Monooleate | 400 | | | | |
| Sodium Bicarbonate + | 1600 | 2000 | 98 | 95 | " |
| Glycerol Monostearate | 400 | | | | |

TEST EXAMPLE 9

(Test for preventing powdery mildew in cucumber plant)

Test Example 5 was repeated except that polyoxyethylene (20) sorbitan monolaurate, glycerol monostearate and diglycerine monooleate were used in the formulation shown in Example 8.

The obtained results are shown in the following.

TABLE 6

| Test Compounds | Concentration (ppm) | Preventing Value 10th day | Preventing Value 14th day | Chemical Injury |
|---|---|---|---|---|
| Sodium | 2000 | 45 | 42 | none |

TABLE 6-continued

| Test Compounds | Concentration (ppm) | Preventing Value 10th day | Preventing Value 14th day | Chemical Injury |
|---|---|---|---|---|
| Bicarbonate Polyoxyethylene (20) Sorbitan Monolaurate | 2000 | 32 | 28 | " |
| Glycerol Monostearate | 2000 | 25 | 16 | " |
| Diglycerine monooleate | 2000 | 28 | 20 | " |
| Sodium Bicarbonate + Polyoxyethylene (20) Sorbitan Monolaurate | 1600 / 400 } 2000 | 98 | 92 | " |
| Sodium Bicarbonate + Glycerol Monostearate | 1600 / 400 } 2000 | 100 | 94 | " |
| Sodium Bicarbonate + Diglycerine Monooleate | 1600 / 400 } 2000 | 100 | 98 | " |

TEST EXAMPLE 10

Test Example 6 was repeated except that sorbitan monolaurate, polyoxyethylene (20) glycerine monostearate and glycerol monooleate were used in the formulation shown in Example 8.

The obtained results are shown in the following.

TABLE 7

| Test Compounds | Concentration (ppm) | Preventing Value (%) | Chemical Injury |
|---|---|---|---|
| Sodium Bicarbonate | 2000 | 66 | none |
| Sorbitan Monolaurate | 2000 | 8 | " |
| Polyoxyethylene (20) Glycerine Monostearate | 2000 | 15 | " |
| Glycerol Monooleate | 2000 | 20 | " |
| Sodium Bicarbonate + Sorbitan Monolaurate | 1600 / 400 } 2000 | 100 | " |
| Sodium Bicarbonate + Polyoxyethylene (20) Glycerine Monostearate | 1600 / 400 } 2000 | 100 | " |
| Sodium Bicarbonate + Glycerine Monooleate | 1600 / 400 } 2000 | 98 | " |

TEST EXAMPLE 11

(Test for preventing stem end rot in oranges)

Test Example 7 was repeated except that glycerol monostearate, propyleneglycol monooleate and sorbitan monolaurate were used in the formulation shown in Example 8. The obtained results are shown in the following.

TABLE 8

| Test Compounds | Concentration (ppm) | Preventing Value (%) | Chemical Injury |
|---|---|---|---|
| Sodium Bicarbonate | 2000 | 68 | none |
| Sorbitan Monolaurate | 2000 | 11 | " |
| Glycerol Monostearate | 2000 | 25 | " |
| Propyleneglycol Monooleate | 2000 | 21 | " |
| Sodium Bicarbonate + Sorbitan Monolaurate | 1600 / 400 } 2000 | 100 | " |

TABLE 8-continued

| Test Compounds | Concentration (ppm) | Preventing Value (%) | Chemical Injury |
|---|---|---|---|
| Sodium Bicarbonate + Glycerol Monostearate | 1600 / 400 } 2000 | 98 | " |
| Sodium Bicarbonate + Propyleneglycol Monooleate | 1600 / 400 } 2000 | 100 | " |

TEST EXAMPLE 12

(Test for preventing sheath blight in rice plant)

Rice plants at the five leaf stage planted in a pot were sprayed by the conventional method with dust containing 20% effective components and prepared according to Example 7. Two hours after spraying, the test fungi (sheath blight fungi; *Pyricularia sasakii*) was inoculated to the rice plants. The inoculation was made by inserting a fungi cluster (punched out in a diameter of 8 mm) into the leaf sheaths of the rice plants. After the treatment, the leaf bases were covered with PVA film, and the rice plants were placed in a greenhouse for seven days and the total lengths of leisions were measured.

On the other hand, sodium bicarbonate and glycerol monostearate were used singly as controls in the same way as in the above, and the total lengths of leisions were also measured. The preventing values were calculated according to the following formula.

$$\text{Preventing value} = \left(1 - \frac{\text{Total length of leisions in treated area}}{\text{Total length of leisions in untreated area}}\right) \times 100$$

TABLE 9

| Test Compounds | Amount of Dust Applied (kg/10a) | Preventing Value (%) | Chemical Injury |
|---|---|---|---|
| Sodium Bicarbonate | 10 | 25 | none |
| Glycerol Monostearate | 5 | 5 | " |
| Sodium Bicarbonate + Glycerol Monostearate | 8 | 96 | " |

TEST EXAMPLE 13

(Test for preventing powdery mildew in strawberry)

Strawberry plants (kind: Harunokaori) cultivated in vinyl hot houses were transplanted to plastic pots having a diameter of 12 cm, and cultivated in a greenhouse. Then in a closed chamber the strawberry plants were artificially wind-inoculated with conidospores of powdery mildew of strawberry (*Sphaerotheca humuli*). A given concentration of components prepared according to Example 4 using glycerol monostearate was sprayed three times at intervals of one week with a glass sprayer in an amount of 30 ml per plant. Immediately before the first spraying with the composition, the surfaces and backs of the leaves were checked, and the surface and backs of the leaves appearing thereafter were checked to calculate the preventing values in terms of the diseased leaf ration and infection ratio. In the same manner, single uses of sodium bicarbonate and glycerol monostearate were tested as controls.

TABLE 10

| Test Chemicals | Concentration (ppm) | Preventing Value (%) | Chemical Injury |
|---|---|---|---|
| Sodium Bicarbonate | 2000 | 50 | none |
| Glycerol Monostearate | 2000 | 7 | " |
| Sodium Bicarbonate + Glycerol Monostearate | 1600 + 400 } 2000 | 98 | " |

TEST EXAMPLE 14

(Test for preventing powdery mildew in Spanish paprika)

To young seedlings of Spanish paprika (kind: Zruho) having ten true leaves, a given concentration of the chemicals (wettable powder prepared according to Example 4 using glycerol monostearate) was uniformly sprayed on the surfaces and backs of the leaves in an amount of 40 ml per two pots. Then conidiums of powdery mildew of Spanish paprika (*Leveilicla taurica*) were artificially wind-inoculated. 2 or 3 weeks after inoculation, the number of leisions formed were counted, and the preventing values were calculated according to the formula of Test Example 1. As contrasts, single uses of sodium bicarbonate and glycerol monostearate were also tested in the same manner.

TABLE 11

| Test Chemicals | Concentration (ppm) | Preventing Value (%) | Chemical Injury |
|---|---|---|---|
| Sodium Bicarbonate | 2000 | 40 | none |
| Glycerol Monostearate | 2000 | 7 | " |
| Sodium Bicarbonate + Glycerol Monostearate | 1600 + 400 } 2000 | 95 | " |

TEST EXAMPLE 15

(Test for preventing powdery mildew in melon)

Melon seedlings (4 true leaves) grown in pots were inoculated with powdery mildew by contacting the leaves with condidium on a stub burst out the disease in a greenhouse. Two days after inoculation, the seedlings were adequately sprayed with a given concentration of chemicals prepared according to Example 4 using glycerol monostearate. The chemicals were sprayed two times at an interval of five days. Five days after the last spraying of chemicals, the number of leisions of the leaves were counted and the preventing values were calculated according to the formula in Test Example 1. As contrasts, single uses of sodium bicarbonate and glycerol monostearate were also tested in the same method.

TABLE 12

| Test Chemicals | Concentration (ppm) | Preventing Value (%) | Chemical Injury |
|---|---|---|---|
| Sodium Bicarbonate | 2000 | 45 | none |
| Glycerol Monostearate | 2000 | 5 | " |
| Sodium Bicarbonate + Glycerol Monostearate |  | 100 | " |

TEST EXAMPLE 16

(Test for preventing orange storage disease)

Test Example 4 was repeated except that the formulation illustrated in Example 13 was used. As contrasts, single uses of sodium bicarbonate and Lecion LP-1 were also tested in the same manner.

The results obtained are shown in the following.

TABLE 13

| Test Chemicals | Concentration (ppm) | Preventing Value 4th day | Preventing Value 6th day | Chemical Injury |
|---|---|---|---|---|
| Sodium Bicarbonate | 3000 | 68 | 65 | none |
| Lecion LP-1 | 1000 | 20 | 18 | " |
| Sodium Bicarbonate + Lecion LP-1 | 3000 + 563 } 3563 | 100 | 100 | " |

The preventing values shown in Table 13 are mean values of those obtained in each block in the treated area. In the case of using sodium bicarbonate and Lecion LP-1 singly, the obtained values varied greatly. On the contrary, the present composition shows a stable preventing value of almost 100%.

TEST EXAMPLE 17

(Test for preventing anthracnose in cucumber plant)

Two weeks old cucumber seedlings of (2 to 3 plants per pot in pots having a diameter of 6.6 cm) were uniformly sprayed with the diluted wettable powder prepared according to Example 12 in an amount of 40 ml per 2 pots. On the other hand, anthracnose of cucumber (*Colletotrichum lagenarium*) was cultured in a slope culture medium at 28° C. for one week to form spores. The spores were suspended in water in a concentration of 100 spores per one field of vision under a microscope at 150 magnifications to prepare a suspension of spores. 50 ml of the suspension of the spores was sprayed with a spray gun on the cucumber seedlings in five blocks, each of which comprised 25 pots. After inoculation, the seedlings were placed in a greenhouse for two days to be infected. 4 to 6 days after infection, the degree of infection was observed.

As control, other seedlings were treated respectively with sodium bicarbonate and Licion P in the same manner as in the above.

The preventing values were calculated according to fhe formula in Example 1.

The obtained results are shown in the following.

TABLE 14

| Test Chemicals | Concentration (ppm) | Preventing Value 4th day | Preventing Value 6th day | Chemical Injury |
|---|---|---|---|---|
| Sodium Bicarbonate | 3000 | 75 | 75 | none |
| Lecion P | 1000 | 20 | 20 | " |
| Sodium Bicarbonate + Lecion P | 3000 + 563 } 3563 | 100 | 100 | " |

The preventing values shown in Table 14 are the mean values obtained for 5 blocks. The results obtained by the sole use of sodium bicarbonate and Lecion P show great variation. On the contrary, the present fungicide shows a preventing value of about 100%.

TEST EXAMPLE 18

(Test for preventing powdery mildew in cucumber)

Test Example 5 was repeated except that the wettable powder prepared according to Example 13 was used.

The obtained results are shown in the following.

TABLE 15

| Test Chemicals | Concentration (ppm) | Preventing Value 10th day | Preventing Value 14th day | Chemical Injury |
|---|---|---|---|---|
| Sodium Bicarbonate | 3000 | 75 | 75 | none |
| Lecion LP-1 | 1000 | 40 | 35 | " |
| Sodium Bicarbonate + Lecion LP-1 | 3000 / 563 } 3563 | 100 | 100 | " |

The preventing values shown in Table 15 are mean values for 5 blocks. The values obtained for the sole use of sodium bicarbonate and Lecion LP-1 are scattered. On the contrary, the present composition shows a stable preventing value of about 100%.

As is clear from the test results in each test example, the mean preventing values obtained for the sole use of sodium bicarbonate and the several kinds of food emulsifiers are about 66% at highest, and tend to decline proportionately to the degree to which the disease has advanced. On the contrary, the present fungicide shows a stable preventing effect and repeatedly sustains a preventing value near 100% even in advanced stages of the disease.

In the above, the invention is examplified in terms of some preferred embodiments, but these embodiments are illustrated with the intension of illustration and without any intention to place limitations on the invention; and the invention is to be construed on the basis of the appended claims.

What is claimed is:

1. An agricultural and horticultural fungicide and fruit storage disease preventing composition, which comprises a fungicidally effective amount of sodium bicarbonate, a food emulsifier and 0–90% based on the total weight of the composition of at least one food compatible carrier, wherein said food emulsifier is at least one member selected from the group consisting of fatty acid glycerol esters, fatty acid sucrose esters, fatty acid sorbitan esters and derivatives thereof, fatty acid propyleneglycol esters and lecithin and wherein the mixing ratio of sodium bicarbonate to said food emulsifier is 1:1 to 20:1 by weight.

2. A composition according to claim 1, wherein said food compatible carrier is selected from the group consisting of starch, dextrin, sodium alginate and sodium caseinate.

3. A composition in wettable powder form according to claim 1, wherein sodium bicarbonate and said food emulsifier are contained in amounts of 10 to 100 percent by weight of total weight and the balance is a carrier.

4. A composition in dust form according to claim 1, wherein sodium bicarbonate and said food emulsifier are contained in amounts of 0.1 to 20 percent by weight of total weight and the balance is said carrier.

5. A process for producing an agricultural and horticultural fungicide and fruit storage disease preventing agent, which comprises dispersing at least one food emulsifier and at least one hydrophilic colloidal substance in warm water, drying the dispersion to form a powder, mixing said powder with a fungicidally effective amount of sodium bicarbonate, and 0–90% based on the total weight of the agent of at least one food compatible carrier, wherein the food emulsifier is at least one member selected from the group consisting of fatty acid glycerol esters, fatty acid sucrose esters, fatty acid sorbitan esters and de4ivatives thereof, fatty acid propyleneglycol esters and lecithin and wherein said sodium bicarbonate and food emulsifier are used in a ratio by weight of 1:1 to 20:1.

6. A process for producing an agricultural and fruit storage disease preventing agent, which consists of dissolving a food emulsifier into a solvent which is a member selected from the group consisting of alcohol, propyleneglycol, glycerol and sorbitol, and spraying or mixing the solution on sodium bicarbonate pwoder in an effective amount of the latter to permit the absorption of the solution by the sodium bicarbonate powder and mixing the resulting powder with 0–90% of a food compatible carrier, wherein the food emulsifier is at least one member selected from the group consisting of fatty acid glycerol esters, fatty acid sucrose esters, fatty acid sorbitan esters and derivatives thereof, fatty acid propyleneglycol esters and lecithin and wherein the sodium bicarbonate and food emulsifier are used in a ratio by weight of 1:1 and 20:1.

7. A process according to claim 5, wherein said hydrophilic colloidal substance is selected from the group consisting of starch, dextrin, carboxymethyl cellulose, sodium alginate and sodium caseinate.

8. A process according to claim 5, wherein said hydrophilic colloidal substance is used in an amount of 5 to 50 percent by weight of the total weight.

9. A process for producing agricultural and horticultural fungicide and fruit storage disease preventing agent in wettable powder form according to claim 5, wherein the effective components, sodium bicarbonate and food emulsifier, are used in an amount of 10 to 90 percent by weight of the total weight of said agent.

10. A process for producing an agricultural, fungicidal and fruit storage disease preventing agent in dust form according to claim 9, wherein the effective compounds, sodium bicarbonate and food emulsifier, are used in an amount of 0.1 to 20 by weight of the total weight of said agent.

11. A process for producing an agricultural and horticultural fungicide and fruit storage disease preventing agent in wettable powder according to claim 6, wherein the effective components, sodium bicarbonate and food emulsifier, are used in an amount of 10 to 90 percent by weight of the total weight of said agent.

12. A process for producing an agricultural and horticultural fungicide and fruit storage disease preventing agent in dust form according to claim 6, wherein the effective components, sodium bicarbonate and food emulsifier are used in an amount of 0.1 to 20 by weight of the total weight of said agent.

* * * * *